United States Patent
Watson et al.

(10) Patent No.: US 10,299,734 B2
(45) Date of Patent: May 28, 2019

(54) MEDICAL DEVICE WITH ADAPTIVE POWER CONSUMPTION

(71) Applicant: COVIDIEN LP, Mansfield, MA (US)

(72) Inventors: James N. Watson, Edinburgh (GB); Daniel Bartlett, Annapolis, MD (US); Paul S. Addison, Edinburgh (GB)

(73) Assignee: Covidien LP, Mansfield, MA (US)

( * ) Notice: Subject to any disclaimer, the term of this patent is extended or adjusted under 35 U.S.C. 154(b) by 133 days.

(21) Appl. No.: 15/281,561

(22) Filed: Sep. 30, 2016

(65) Prior Publication Data

US 2017/0095215 A1 Apr. 6, 2017

Related U.S. Application Data

(60) Provisional application No. 62/236,270, filed on Oct. 2, 2015.

(51) Int. Cl.
| | |
|---|---|
| *A61B 5/0205* | (2006.01) |
| *A61B 5/00* | (2006.01) |
| *A61B 5/1455* | (2006.01) |
| *A61B 5/024* | (2006.01) |
| *A61B 5/08* | (2006.01) |
| *A61B 5/11* | (2006.01) |

(52) U.S. Cl.
CPC ............ *A61B 5/721* (2013.01); *A61B 5/0002* (2013.01); *A61B 5/0205* (2013.01); *A61B 5/02416* (2013.01); *A61B 5/02438* (2013.01); *A61B 5/14551* (2013.01); *A61B 5/7285* (2013.01); *A61B 5/0816* (2013.01); *A61B 5/1123* (2013.01); *A61B 2560/0209* (2013.01); *A61B 2560/0214* (2013.01)

(58) Field of Classification Search
CPC .. A61B 5/721; A61B 5/02416; A61B 5/14551
See application file for complete search history.

(56) References Cited

U.S. PATENT DOCUMENTS

| | | | | |
|---|---|---|---|---|
| 5,025,791 | A * | 6/1991 | Niwa | A61B 5/14552 600/324 |
| 7,018,338 | B2 * | 3/2006 | Vetter | A61B 5/02416 600/479 |

(Continued)

OTHER PUBLICATIONS

Yousefi et al. "A Motion-Tolerant Adaptive Algorithm for Wearable Photoplethysmographic Biosensors." IEEE Journal of Biomedical and Health Informatics (vol. 18, Issue: 2, Mar. 2014), pp. 670-681.*

(Continued)

*Primary Examiner* — Meredith Weare
(74) *Attorney, Agent, or Firm* — Fletcher Yoder PC

(57) ABSTRACT

A system may include a photoplethysmograph (PPG) sensor configured to be secured to a patient and to generate a PPG signal for the patient. The system may also include a motion sensor configured to generate a motion signal indicative of motion of the patient. Further, the system may include a controller configured to receive the PPG signal from the PPG sensor and the motion signal from the motion sensor, to analyze the motion signal to detect motion of the patient, and to deactivate the at least one emitter of the PPG sensor based on the analysis of the motion signal when motion of the patient is detected.

16 Claims, 8 Drawing Sheets

(56) References Cited

U.S. PATENT DOCUMENTS

| | | | |
|---|---|---|---|
| 2003/0065269 A1* | 4/2003 | Vetter | A61B 5/02416 600/503 |
| 2004/0034294 A1* | 2/2004 | Kimball | A61B 5/02125 600/323 |
| 2004/0260186 A1 | 12/2004 | Dekker | |
| 2005/0049470 A1* | 3/2005 | Terry | A61B 5/14552 600/323 |
| 2009/0312612 A1* | 12/2009 | Rantala | A61B 5/0205 600/301 |
| 2010/0016676 A1* | 1/2010 | Addison | A61B 5/14551 600/300 |
| 2010/0324384 A1* | 12/2010 | Moon | A61B 5/1118 600/323 |
| 2012/0123226 A1* | 5/2012 | Schwenk | A61B 5/1118 600/301 |
| 2012/0253141 A1* | 10/2012 | Addison | A61B 5/14551 600/301 |
| 2012/0310587 A1* | 12/2012 | Tu | G01D 1/16 702/141 |

OTHER PUBLICATIONS

Tobin, Robert M., Pologe, Jonas A., Batchelder, Paul B., A Characterization of Motion Affecting Pulse Oximetry in 350 Patients. Anesthesia & Analgesia, 2002, pp. 1-17.

* cited by examiner

MEDICAL DEVICE WITH ADAPTIVE POWER CONSUMPTION

CROSS-REFERENCE TO RELATED APPLICATIONS

The present application claims priority to and the benefit of U.S. Provisional Application No. 62/236,270, which was filed on Oct. 2, 2015, and entitled "Medical Device with Adaptive Power Consumption," the disclosure of which is hereby incorporated by reference in its entirety for all purposes.

BACKGROUND

The present disclosure relates generally to medical devices for monitoring physiological parameters of a patient and, more particularly, to techniques for reducing power consumption of medical devices.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring certain physiological characteristics of a patient. Such devices provide doctors and other healthcare personnel with the information they need to provide the best possible healthcare for their patients. As a result, such monitoring devices have become an indispensable part of modern medicine. For example, photoplethysmography is a common technique for monitoring physiological characteristics of a patient, and one device based upon photoplethysmography techniques is typically referred to as a pulse oximeter. Pulse oximeters may be used to measure and monitor various blood flow characteristics of a patient. A pulse oximeter may be utilized to monitor the blood oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time-varying amount of arterial blood in the tissue during each cardiac cycle.

A patient in a hospital setting may be monitored by a variety of medical devices, including devices based on photoplethysmography techniques. For example, a photoplethsymography (PPG) sensor acquires a photoplethsymographic (PPG) signal from a patient, and a patient monitor may use the PPG signal to determine one or more physiological parameters of the patient, such as, for example, blood oxygen saturation, pulse rate, and respiration rate. However, during periods of patient motion, the PPG signal may include artifacts and may have a low signal quality. For example, patient motion may cause optical components of the PPG sensor to lose contact with the skin, which may result in changes to the emitted and/or detected light and may result in signal artifacts and a decreased signal quality. Typically, the signal quality of the PPG signal or the signal quality of the physiological parameter determined based on the PPG signal is assessed, and the determined physiological parameter is weighted based on the signal quality and used in an algorithm to update the physiological parameter (e.g., on a display). However, if the signal quality is below a signal quality threshold, the determined physiological parameter may be zero weighted and, as a result, may not be used in the algorithm to update the physiological parameter. As such, the PPG signal may not provide useful information during periods of motion.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
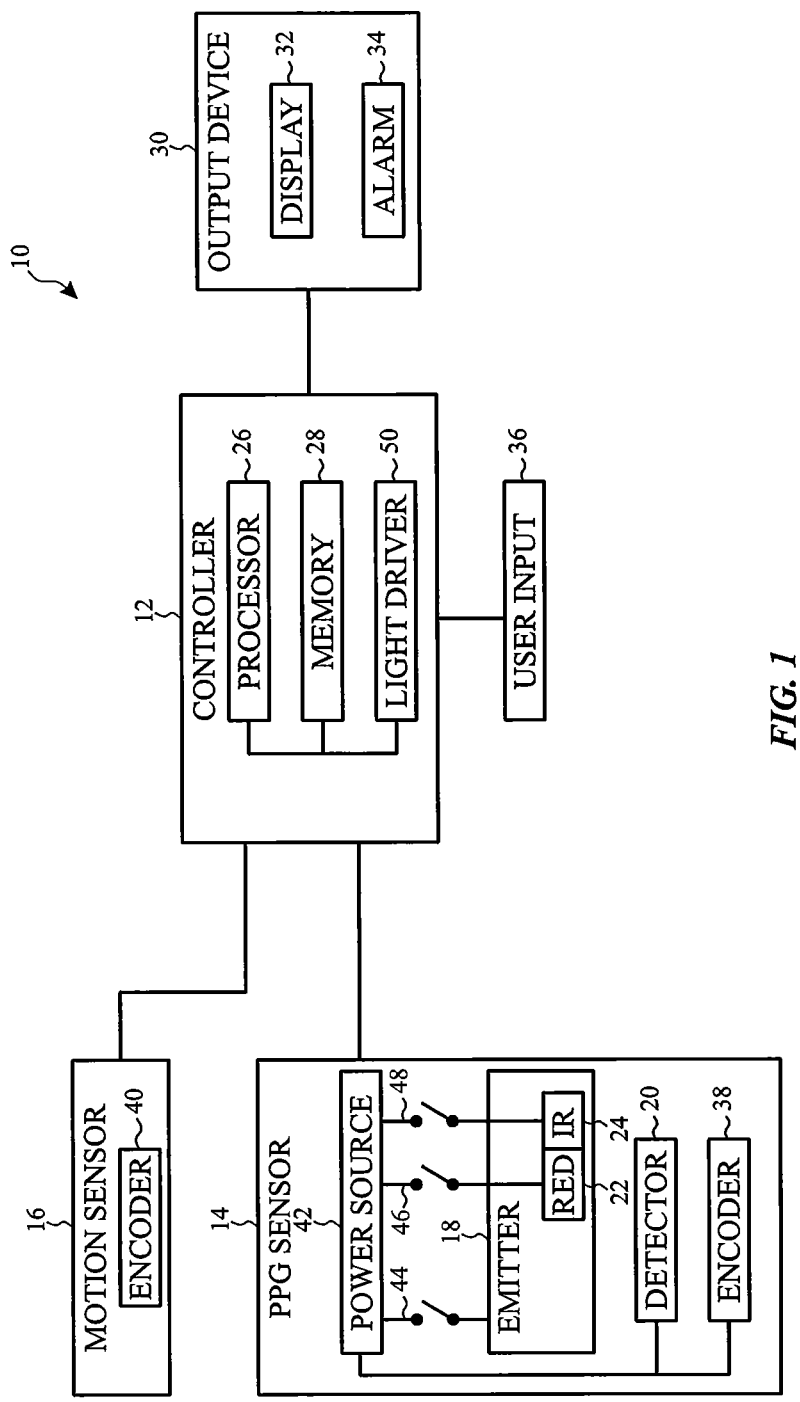
FIG. 1 is a block diagram of components of a medical monitoring system for implementing adaptive power consumption techniques, in accordance with an embodiment of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Provided herein are techniques for reducing the power consumption of a medical device, such as a PPG sensor and/or a PPG monitor. As discussed in greater detail below, the present disclosure relates to systems and methods for obtaining a PPG signal from a PPG sensor coupled to a patient, obtaining a motion signal indicative of motion of the patient from a motion sensor, and adaptively suppressing PPG signal acquisition and/or processing based at least in part on the motion signal to reduce power consumption of the PPG sensor, the PPG monitor, or both. For example, some embodiments relate to techniques for adaptively suppressing PPG signal acquisition by powering off one or more emitters of the PPG sensor based at least in part on the motion signal. For example, a controller may analyze the motion signal to detect patient motion and may turn off (e.g., power off, deactivate, suppress or halt power to, etc.) one or more components of the PPG sensor, such as one or more emitters (e.g., light emitting diodes (LEDs)) and/or one or more detectors, if a duration or degree (e.g., severity) of patient motion exceeds a respective motion threshold. The controller may resume the flow of power to or reactivate the one or more LEDs in response to a determination that the patient motion has ceased or is less than a motion threshold. In some embodiments, the controller may turn off or deactivate the one or more LEDs for a predetermined period. For example, in some embodiments, the controller may reactivate the one or more LEDs after the predetermined period even if patient motion has not ceased or is not less than a motion threshold, so that physiological parameters determined from a prior PPG signal (e.g., before patient motion is detected) are not relied on for too long. Thus, in contrast to techniques in which the LEDs of a PPG sensor are driven during periods of motion when the signal quality of the PPG signal may be below a signal quality threshold and may not provide useful information for patient monitoring, the present techniques may reduce power consumption of the PPG sensor and/or the PPG monitor by powering off one or more components of the PPG sensor (e.g., emitters and/or detectors) during periods of motion.

In certain embodiments, the controller may classify the type of patient motion and may use type of patient motion as a factor in determining whether to suppress PPG signal acquisition and/or processing. For example, different types of patient motion may affect the PPG signal differently and, in particular, may cause different signal artifacts and/or different changes in the signal quality of the PPG signal. Further, in some embodiments, multiple physiological parameters may be determined based on the PPG signal, such as, for example, oxygen saturation, pulse rate, and/or respiration rate, and the different types of patient motion may have different effects on the accuracy of the calculation of the different physiological parameters. Accordingly, in some embodiments, the controller may be configured to selectively suppress PPG signal acquisition and/or processing based on the type of patient motion. As such, the present techniques may reduce power consumption by adaptively suppressing the PPG signal acquisition and/or processing when the PPG signal is noisy and/or when the physiological parameters determined from the PPG signal may be inaccurate due to particular types of patient motion.

With the foregoing in mind, FIG. 1 illustrates a medical monitoring system 10 that may be implemented with adaptive power consumption techniques. As shown, the system 10 may include a controller 12 that may be used in conjunction with a PPG sensor 14 and a motion sensor 16. In some embodiments, the controller 12 may be a medical monitor, such as a standalone medical monitor, a multi-parameter monitor, or may be part of a distributed monitoring system under control of a central station (e.g., a central processing device). In certain embodiments, the controller 12 may be incorporated into (e.g., disposed in a housing of) the PPG sensor 14 or the motion sensor 16. In other embodiments, the controller 12 may be any suitable processor-based device, such as, but not limited to, computer workstation, a server, a desktop, a notebook, a laptop, a handheld computer, a mobile device, or the like.

The controller 12 may be coupled to the PPG sensor 14 for monitoring one or more physiological parameters of a patient. For example, the controller 12 may receive a PPG signal from the PPG sensor 14, and the controller 12 may be configured to generate a physiological waveform and/or calculate or measure one or more physiological parameters based on the PPG signal. In certain embodiments, the controller 12 may be configured to calculate oxygen saturation, regional oxygen saturation, pulse rate, respiration rate, glucose/insulin concentration, blood pressure, cerebral autoregulation, and/or any other suitable physiological parameter based on the PPG signal. Further, it should be appreciated that the controller 12 may be used in conjunction with a variety of medical monitors and medical sensors to conduct a variety of medical measurements.

The PPG sensor 14 may be any suitable sensor configured to acquire a PPG signal from a patient. The PPG sensor 14 may be configured to acquire a PPG signal from any suitable location on a patient, such as, for example, a digit (e.g., a finger or a toe), the forehead, an ear, the stomach, and the like. In certain embodiments, the PPG sensor 14 may be a pulse oximetry sensor or a regional oximetry sensor. As illustrated, the PPG sensor 14 may include at least one emitter 18 configured to emit light and at least one detector 20 configured to detect light after interaction with tissue of a patient and to generate PPG signals based on the detected light. In certain embodiments, the emitter 18 may include one or more light emitting diodes (LEDs), which may be configured to emit at different wavelengths of light. For example, the emitter 18 may include a red LED 22 configured to emit red light and an infrared LED 24 configured to emit infrared or near infrared light.

The controller 12 may include a processor 26 configured to execute code (e.g., stored in a memory 28 of the controller 12 or received from another device) for filtering and processing the PPG signals received from the PPG sensor 14 to calculate physiological parameters, such as oxygen saturation, regional oxygen saturation, pulse rate, respiration rate, and the like. Additionally, in certain embodiments, the system 10 may include an output device 30, which may receive signals from the controller 12 and may visually and/or audibly output information indicative of the information from the signals. For example, the output device 30 may include a display 32 and an alarm 34 (e.g., speaker). In some embodiments, the controller 12 may include the output device 30 (e.g., may be supported by the same housing). In other embodiments, the output device 30 may be separate from the controller 12. The output device 30 may be any suitable device for conveying information from the signals received from the controller 12, including a computer workstation, a server, a desktop, a notebook, a laptop, a handheld computer, a mobile device, or the like. Additionally, the controller 12 may be operatively coupled to a user input device 36, which may receive inputs from a user. For example, the user input device 36 may include a keyboard, one or more buttons, a touch-screen display, or a combination thereof. The controller 12 may include the user input device 36 or the user input device 36 may be separate from the controller 12.

Additionally, the controller 12 may be coupled the motion sensor 16 for monitoring motion of the patient. While the illustrated embodiment shows one motion sensor 16, it should be appreciated that any suitable number of motion sensors 16 may be used, such as two, three, four, five, or more. Further, as will be described in more detail below, the PPG sensor 14 and the motion sensor 16 may disposed in the same location or different locations. For example, in certain embodiments, the PPG sensor 14 and the motion sensor 16 may each be placed on the same part of the patient's body. Indeed, in some embodiments, the PPG sensor 14 and the motion sensor 16 may be part of the same sensor or supported by a single sensor housing. For example, the PPG sensor 14 and the motion sensor 16 may be part of an integrated PPG system configured to measure patient motion and physiological parameters, such as, for example, oxygen saturation, regional oxygen saturation, pulse rate, and/or respiration rate.

In some embodiments, the PPG sensor 14 and the motion sensor 16 may include separate housings. For example, as will be described in more detail below, the motion sensor 16 may be disposed in a housing of a patient-worn medical monitor (e.g., patient-worn pulse oximeter, Zephyr™ Bio-Harness™, etc.), which may be operatively coupled to the PPG sensor 14. In some embodiments, as will be described in more detail below, the motion sensor 16 may be disposed in a patient-worn article, such as, for example, a strap (e.g., a wrist strap, a chest strap, an ankle strap), a bracelet, clothing, a garment, a harness, a ring, a necklace, etc. Additionally, as will be described in more detail below, the motion sensor 16 may be disposed in a patient device, such as a patient bed, a wheelchair, a pillow, a blanket, and the like.

The motion sensor 16 may be any suitable sensor configured to generate a signal indicative of the motion of the patient (i.e., the patient monitored by the PPG sensor 14). For example, the motion sensor 16 may be configured to generate a signal indicative of the acceleration, velocity and/or position of the patient or specific areas of the patient (e.g., a digit, a hand, an arm, a leg, a wrist, an ankle, the head, the chest, etc.). The motion sensor 16 may be configured to generate one or more signals related to the acceleration and/or velocity of the patient or specific areas of the patient in one dimension (e.g., the x-axis, the y-axis, or the z-axis), two dimensions (e.g., two of the x-axis, the y-axis, or the z-axis), or three dimensions (e.g., the x-axis, the y-axis, and the z-axis). In certain embodiments, the motion sensor 16 may generate a motion signal including one or more components representing one or more axis of motion.

In some embodiments, the motion sensor 16 may include an accelerometer, such as, for example, a piezoelectric device, piezoresistive device, and/or a capacitive device that may convert mechanical motion into an electrical signal. In some embodiments, the motion sensor 16 may include an optical, microwave, or acoustic detector that may detect changes in the optical, microwave, or acoustic field cause by patient motion. The motion sensor 16 may be active or passive. In certain embodiments, the motion sensor 16 may include a camera, such as a video camera. In some embodiments, the motion sensor 16 may also include a processor, memory, and/or any other suitable software and/or hardware components to process a video signal obtained by the motion sensor 16 and detect patient motion based on the video signal. Regardless of its form, the motion sensor 16 may be configured to generate a motion signal indicative of motion of the patient or motion of one or more specific areas of the patient (e.g., a digit, a hand, an arm, a leg, a wrist, an ankle, the head, the chest, etc.) over time.

The motion sensor 16 may provide the motion signal to the controller 12, or to any other suitable processing device, to enable detection of patient motion, determination of the degree of patient motion, determination of the duration of patient motion, and/or determination of the type of patient motion. For example, in certain embodiments, the processor 26 may be configured to execute code (e.g., stored in the memory 28 of the controller 12 or received from another device) for filtering and processing the motion signal received from the motion sensor 16 to detect patient motion, to determine the degree and/or duration of patient motion, and/or to determine (e.g., classify) the type of patient motion. In certain embodiments, the processor 26 may be configured to analyze a raw or processed (e.g., filtered) motion signal. In other embodiments, the processor 26 may be configured to integrate a raw or processed motion signal to generate a velocity or displacement signal. Further, in some embodiments, the processor 26 may be configured to decompose the motion signal into component parts using any suitable signal transform methods, such as, for example, fast Fourier transform, discrete Fourier transform, wavelet transform, Hilbert transform, or Laplace transform. For example, the processor 26 may decompose the motion signal into one or more component parts where each component part represents an axis of motion (e.g., x-axis, y-axis, or z-axis).

Additionally, in some embodiments, the processor 26 may be configured to classify the motion signal into degrees and/or types of motion using neural networks (e.g., multi-layer perception networks (MLP) or radial basis networks), stochastic or probabilistic classifiers (e.g., Bayesian, Hidden Markov Model (HMM), or fuzzy logic classifiers), propositional or predicate logics (e.g., non-monotonic or modal logics), nearest neighbor classification methods (e.g., $k^{th}$ nearest neighbor or learning vector quantization (LVQ) methods), or any other learning-based algorithms. For example, the processor 26 may implement any suitable processing techniques to classify the motion signal into types of patient motion such as, for example, walking, tapping (e.g., tapping on the PPG sensor 14), bending (e.g., bending of the tissue site proximate to the PPG sensor 14), rolling (e.g., rolling over in bed), kicking, and the like.

Further, the memory 28 may store one or more thresholds that may be used by the processor 26 to detect patient motion. For example, the memory 28 may store one or more motion thresholds for the motion signal, and the processor 26 may detect patient motion when the motion signal violates (e.g., is greater than or less than) the one or more motion thresholds. In one embodiment, a motion threshold to detect patient motion may be 0, such that the processor 26 detects patient motion in response to any movement of the patient detected by the motion sensor 16. In some embodiments, the motion threshold may be selected to such that certain movements (e.g., small movements or movements that may not affect the signal quality of the PPG signal) may not violate the motion threshold and thus, are not detected as patient motion by the processor 26. For example, a motion threshold 16 may be disposed in a chest strap worn by a patient, and the motion threshold may be selected such that processor 26 does not detect patient motion in response to motion due to breathing of the patient and does detect patient motion in response to various other motions, such as walking or rolling in bed.

The memory 28 may also store one or more thresholds that may be used by the processor 26 to determine when to suppress PPG signal acquisition and/or processing. In some embodiments, the processor 26 may suppress PPG signal acquisition and/or processing in response to any detected motion. For example, the processor 26 may suppress PPG signal acquisition and/or processing when the motion signal violates the motion threshold used to detect patient motion. In some embodiments, the processor 26 may suppress PPG signal acquisition and/or processing based on the degree or severity of patient motion or based on the duration of patient motion (e.g., less severe patient motion). That is, in some embodiments, the processor 26 may not suppress PPG signal acquisition and/or processing in response to detected patient motion if the patient motion is relatively minimal and quick.

Accordingly, the memory 28 may store one or more motion degree thresholds' (e.g., motion severity thresholds), and the processor 26 may suppress PPG signal acquisition and/or processing in response to a determination that the motion signal violated (e.g., was greater than or less than) a motion degree threshold. For example, severe patient motion (e.g., when the motion signal violates the motion degree threshold) may reduce the signal quality of the PPG signal and/or reduce the accuracy of physiological parameters calculated from the PPG signal. The memory 28 may also store one or more duration thresholds, and the processor 26 may suppress PPG signal acquisition and/or processing in response to a determination that the motion signal violated a threshold (e.g., the motion threshold to detect patient motion or any other suitable threshold) for an amount of time exceeding a duration threshold. For example, prolonged, less severe patient motion (e.g., when detected patient motion violates the duration threshold) may reduce the signal quality of the PPG signal and/or reduce the accuracy of physiological parameters calculated from the PPG signal. In some embodiments, the duration threshold may be between approximately 5 seconds and 5 minutes, 10 seconds and 4 minutes, 20 seconds and 3 minutes, or 30 seconds and 2 minutes.

The one or more thresholds (e.g., motion thresholds, motion degree thresholds, duration thresholds, etc.) may be based on characteristics of the motion sensor 16, characteristics of the PPG sensor 14, characteristics of the patient, or a combination thereof. For example, the PPG sensor 14 may include an encoder 38 (e.g., a memory device), which may contain information about the PPG sensor 14, such as what type of sensor it is (e.g., a reflectance or transmittance sensor, an adult sensor, a pediatric sensor, a neonatal sensor, a wrist-worn sensor, a bandage-type sensor, a clip-type sensor, etc.), an intended location of the sensor (e.g., forehead, digit, etc.), the wavelengths of light emitted by the emitter 18, calibration coefficients, algorithms for calculating physiological parameters, and so forth. In some embodiments, the encoder 38 may also store information about the patient, such as age, weight, condition, diagnosis, and so forth. The processor 26 may receive and decode, if necessary, information from the encoder 38 and may use the information to select appropriate thresholds from the memory 28.

Further, in some embodiments, the motion sensor 16 may include an encoder 40 (e.g., a memory device), which may include information about the motion sensor 16, such as what type of sensor it is (e.g., an accelerometer, a piezoelectric device, piezoresistive device, a capacitive device, an optical detector, a microwave detector, an acoustic detector, a camera, a video camera, etc.), an intended location of the motion sensor 16 (e.g., in a housing of the PPG sensor 14, in a patient-worn monitor, in a patient-worn article, in a patient device, a specific area about the patient, etc.). Accordingly, the processor 26 may receive and decode, if necessary, information from the encoder 40 and may use the information to select appropriate thresholds from the memory 28.

Additionally, in some embodiments, the memory 28 may store different thresholds (e.g., motion thresholds, motion degree thresholds, motion duration thresholds, etc.) for different types of patient motion. For example, the memory 28 may store a first threshold that is associated with a first type of motion, and a second threshold that is associated with a second type of motion. Accordingly, the processor 26 may select a threshold based on the type of patient motion.

Further, in some embodiments, the memory 28 may store one or more motion profiles, and the processor 26 may compare the motion signal to the one or more motion profiles to detect patient motion, determine a degree (e.g., severity) of patient motion, and/or determine a type of patient motion. In some embodiments, the one or more motion profiles may be empirically determined. The motion profiles may be based on the type of motion sensor 16. Accordingly, in some embodiments, the memory 26 may store different motion profiles for different types of motion sensors 16, and the processor 26 may select an appropriate motion profile based on the type of motion sensor 16. The motion profiles may include one or more baseline motion profiles indicative of no patient motion or a negligible amount of patient motion. In some embodiments, the motion profiles may include one or more motion profiles indicative of low patient motion, one or more motion profiles indicative of moderate patient motion, one or more motion profiles indicative of high patient motion, or a combination thereof. Accordingly, in some embodiments, the processor 26 may compare the motion signal to the one or more motion profiles indicative of no motion, low motion, moderate motion, and/or high motion to detect patient motion and/or a degree of patient motion. Further, in some embodiments, the memory 28 may store one or more motion profiles indicative of a type of patient motion (e.g., walking, tapping, bending, rolling, kicking, etc.), and the processor 26 may compare the motion signal to the one or more motion profiles indicative of a type of patient motion to determine the type of patient motion.

Additionally, the memory 28 may store one or more suppression thresholds for one or more durations of PPG signal acquisition suppression. For example, the processor 26 may continue monitoring the motion signal during PPG signal acquisition suppression and may resume PPG signal acquisition if patient motion has ceased or if a degree (e.g., severity) or duration or the patient motion no longer violates a respective threshold. However, it may be desirable to resume PPG signal acquisition after a certain amount of time even if the patient motion has not ceased or the patient motion still violates a threshold. In particular, during PPG signal acquisition suppression, the display 32 may not display updated physiological parameter values, and it may be undesirable to rely on prior physiological parameter values that are held on the display 32 during the PPG signal acquisition for too long. Accordingly, in some embodiments, the suppression thresholds may be a maximum amount of time for PPG signal acquisition suppression if patient motion has not ceased or still violates a threshold. In particular, the processor 26 may select a suppression threshold from the memory 28, may suppress PPG signal acquisition based on an assessment of patient motion for a period of time, and may resume PPG signal acquisition when patient motion has ceased, when patient motion no longer violates a threshold, or when the period of time is equal to or greater than the suppression threshold. In one embodiment, the processor 26 may suppress PPG signal acquisition until the suppression threshold is reached even if patient motion ceased before the suppression threshold is reached.

The one or more suppression thresholds may be based on a type of patient monitoring and/or information about a patient, such as age and condition. Accordingly, the processor 26 may use information from the encoder 38 of the PPG sensor 14 to select an appropriate suppression threshold. In some embodiments, the memory 28 may store different suppression thresholds for different types of patient motion. For example, the memory 28 may store a first suppression threshold associated with a first type of patient motion and a second suppression threshold associated with a second type of patient motion. Accordingly, the processor 26 may select a suppression threshold based on the type of patient motion. In some embodiments, a suppression threshold may be between approximately 5 seconds and 5 minutes, 10 seconds and 4 minutes, 20 seconds and 3 minutes, or 30 seconds and 2 minutes.

In some embodiments, a user may input information using the user input device 36, and the processor 26 may use the information from the user input device 36 to select one or more thresholds from the memory 28, such as motion thresholds, motion degree thresholds, motion duration thresholds, suppression thresholds, etc. Additionally, the processor 26 may use the information to select one or more motion profiles. For example, the user may input information about the PPG sensor 14, information about the motion sensor 16, information about the patient, etc. In certain embodiments, a user may input one or more thresholds, such as motion thresholds, motion duration thresholds, motion degree threshold, suppression thresholds, etc.

As described in detail above, the processor 26 may analyze the motion signal using various processing techniques, motion profiles, thresholds, or a combination thereof, to determine when a degree (e.g., severity) of patient motion violates a motion degree threshold and/or when a duration of patient motion (e.g., less severe patient motion) violates a motion duration threshold. To conserve power, the processor 26 may adaptively suppress PPG signal acquisition based on an analysis of the motion signal. In particular, the processor 26 may adaptively suppress PPG signal acquisition when a degree of patient motion violates a motion degree threshold and/or when a duration of patient motion violates a motion duration threshold. To suppress PPG signal acquisition, the processor 26 may turn off (e.g., power off, deactivate, halt flow of power to, etc.) one or more of the emitters 18 of the PPG sensor 14 (e.g., one or both of the LEDs 22 and 24). As used herein, the emitters 18, the red LED 22, and the infrared LED 24 emit light when activated or in an "on" state and do not emit light when deactivated or in an "off" state. In some embodiments, the processor 26 may suppress PPG signal acquisition by deactivating one LED (e.g., the LED 22) of the PPG sensor 14, while still receiving the PPG signal from the PPG sensor 14 resulting from light emitted by the another LED (e.g., the LED 24) of the PPG sensor 14. In other embodiments, the processor 26 may suppress or halt PPG signal acquisition by deactivating all emitters 18 (e.g., the LED 22 and the LED 24) of the PPG sensor 14.

In some embodiments, the PPG sensor 14 may be coupled to at least one power source 42, and the processor 26 may suppress or halt the flow of power from the at least one power source 42 to the one or more emitters 18 (e.g., to one or both of the LEDs 22 and 24) to suppress PPG signal acquisition. In some embodiments, the processor 26 may also suppress the flow of power from the at least one power source 42 to other components of the PPG sensor 14 (e.g., the detector 20) and/or to the PPG sensor 14 (e.g., all components). The power source 42 may be a battery (e.g., a rechargeable battery), AC power (e.g., from an electrical outlet), or any other suitable source of power. As illustrated, the power source 42 may be a component of the PPG sensor 14 (e.g., disposed in a housing of the PPG sensor 14). In some embodiments, the controller 12 may include the power source 42 or may be operatively coupled to the power source 42. For example, the controller 12 may provide power to the PPG sensor 14 via a cable. In such embodiments, the processor 26 may suppress or halt flow of power from the controller 12 to the PPG sensor 14.

In certain embodiments, the system 10 may include at least one switch 44 electrically coupled to and disposed between the power source 42 and the PPG sensor 14. The processor 26 may open the at least one switch 44 to suppress or halt flow of power from the power source 42 to the PPG sensor 14 and may close the at least one switch 44 to resume flow of power to the PPG sensor 14. That is, some embodiments, the at least one switch 44 may halt flow of power to all of the components of the PPG sensor 14. In some embodiments, the at least one switch 44 may only halt flow of power to (e.g., turn off, deactivate, etc.) one or more of the emitters 18. The at least one switch 44 may be a component of the PPG sensor 14 (e.g., disposed in a housing of the PPG sensor 14), as illustrated, or may be separate from the PPG sensor 14. To enable selective suppression of the red LED 22, the infrared LED 24, or both, the at least one switch 44 may include a first switch 46 electrically coupled to and disposed between the power source 42 and the red LED 22 and a second switch 48 electrically coupled to and disposed between the power source 42 and the infrared LED 24. Thus, the processor 26 may selectively open and close the first and second switches 46 and 48 to selectively suppress power to (e.g., turn off, deactivate, etc.) the red LED 22, the infrared LED 24, or both.

In certain embodiments, the controller 12 may provide a drive signal to one or more of the emitters 18 of the PPG sensor 14 (e.g., one or both of the LEDs 22 and 24) that activates the one or more emitters 18 to cause the one or more emitters 18 to emit light. For example, the controller 12 may include a light drive (e.g., an LED driver) 50 that may provide drive signals to selectively activate or turn on the one or more emitters 18. In some embodiments, the processor 26 may modify the drive signal or may suppress the drive signal to selectively turn off or deactivate one or more of the emitters 18 of the PPG sensor 14 (e.g., one or both of the LEDs 22 and 24) to suppress PPG signal acquisition. In some embodiments, the LED driver 50 may provide a time-multiplexed drive signal to the one or more emitters 18. For example, the LED driver 50 may provide a time-multiplexed drive signal to alternate activation of the red LED 22 during red pulse width periods and the IR LED 24 during IR pulse width periods.

Further, in some embodiments, the controller 12 may include detector acquisition circuitry configured to acquire the PPG signal from the detector 20, and the controller 12 may suppress the detector acquisition circuitry during PPG signal acquisition suppression. For example, the detector 20 may still generate the PPG signal in response to detected ambient light when the emitters 18 are deactivated. Accordingly, it may be desirable to suppress the detector acquisition circuitry so that the controller 12 does not receive the PPG signal from the detector 20 when the emitters 18 are deactivated because the resulting PPG signal will not include useful information for calculating physiological parameters.

In some embodiments, the processor 26 may instruct the display 32 to display historical values of physiological parameters when PPG signal acquisition is suppressed. For example, the processor 26 may instruct the display 32 to display the most recent values of the physiological parameters before the processor 26 suppressed PPG signal acquisition. Further, the processor 26 may instruct the display 32 to display the most recent values for the duration of PPG signal acquisition suppression. In certain embodiments, the processor 26 may instruct the display 32 to cease display of physiological parameter values during PPG signal acquisition suppression. It should be appreciated that the processor 26 may provide instructions relating to the physiological parameters determined from the PPG signal, such as oxygen saturation, regional oxygen saturation, pulse rate, hemoglobin, respiration rate, water fraction, and so forth, and the display 32 may continue normal display of other physiological parameters that were not determined from the PPG signal. Further, in some embodiments, the processor 26 may cause the display 32 to display an indicator indicative of PPG signal acquisition suppression.

Additionally, the processor 26 may adaptively suppress PPG signal processing when a degree and/or duration of patient motion violates a threshold. In some embodiments, the processor 26 may adaptively suppress PPG signal processing based on the type of patient motion. For example, different types of patient motion may affect the PPG signal differently and, in particular, may cause different signal artifacts and/or different changes in the signal quality of the PPG signal. Further, multiple physiological parameters may be determined based on the PPG signal, such as, for example, oxygen saturation, pulse rate, and/or respiration rate, and the different types of patient motion may have different effects on the accuracy of the calculation of the different physiological parameters.

For example, a tapping motion on the PPG sensor 14 may have a low negative effect on the accuracy of the algorithm for calculating respiration rate and a high negative effect on the accuracy of the algorithms for calculating oxygen saturation and pulse rate. Accordingly, in some embodiments, the processor 26 may be configured to selectively suppress the PPG signal processing by only processing the PPG signal to determine respiration rate. Further, respiration rate may be determined using only one LED, while oxygen saturation and pulse rate may use two LEDs. Accordingly, the processor 26 may also selectively suppress PPG signal acquisition to turn off or deactivate one LED of the PPG sensor 14 when a tapping motion is present. Additionally, walking may have a high negative effect on the accuracy of the algorithm for calculating respiration rate and a low negative effect on the accuracy of the algorithms for calculating oxygen saturation and pulse rate. Accordingly, in some embodiments, the processor 26 may be configured to process the PPG signal for the calculation of oxygen saturation and pulse rate, while suppressing the PPG signal processing for the calculation of respiration rate.

Figure 2:
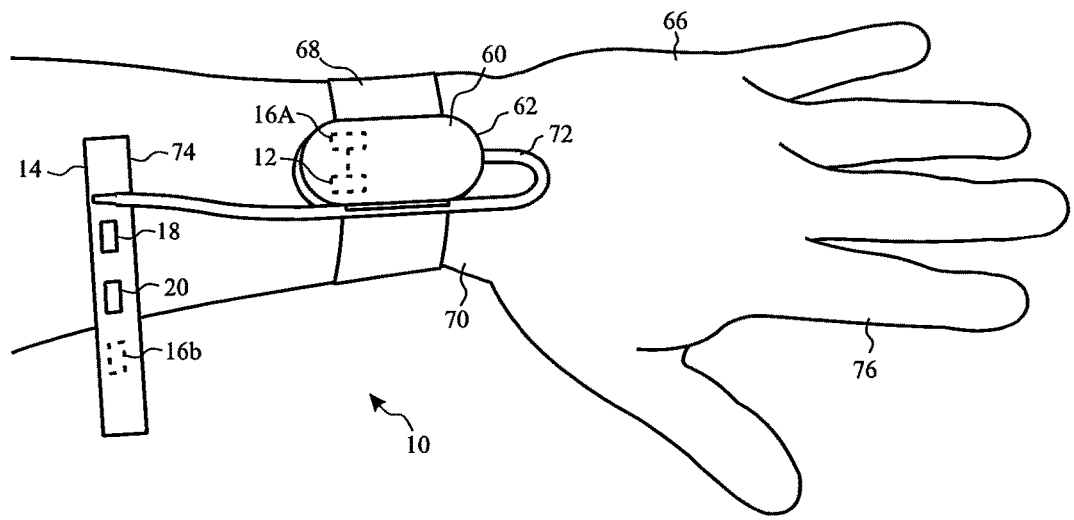
FIG. 2 is a schematic diagram of a patient-worn monitor including a first motion sensor and a PPG sensor including a second motion sensor, in accordance with an embodiment of the present disclosure.

As noted above, the motion sensor 16 may be coupled to the patient. For example, FIG. 2 illustrates an embodiment of the system 10 including a motion sensor 16 (e.g., motion sensor 16*a*) that is disposed in a patient-worn monitor 60. The patient-worn monitor 60 may be any suitable medical device configured to monitor one or more physiological parameters of the patient. For example, the patient-worn monitor 60 may include a pulse oximeter, a heart rate monitor, such as a Zephyr™ BioHarness™, and so forth. In some embodiments, the controller 12 may be operatively coupled to the patient-worn monitor 60 to receive motion signals from the motion sensor 16*a*. In certain embodiments, the patient-worn monitor 60 may include the controller 12. For example, the controller 12 may be disposed in a housing 62 of the patient-worn monitor 60. The housing 62 may be configured to be disposed about and/or secured to a patient 66. For example, in certain embodiments, the housing 62 may include a strap, a bracelet, or any other suitable structure that may be configured to wrap around or otherwise attach to a body part of the patient such as, for example, a wrist, an arm, an ankle, the chest, the forehead, or the like. In some embodiments, the housing 62 may be disposed about and/or secured to the patient 66 via an attachment member 68, which may include a strap, a bracelet, or any other suitable structure that may be configured to wrap around or otherwise attach to a body part of the patient such as, for example, a wrist, an arm, an ankle, the chest, the forehead, or the like.

As illustrated, the motion sensor 16*a* is disposed in the housing 62 of the patient-worn monitor 60. As such, the motion sensor 16*a* may generate motion signals corresponding to movement of the body part to which the housing 62 is secured. For example, as illustrated, the housing 62 may be secured about a wrist 70 of the patient 66. In such embodiments, the motion sensor 16*a* may generate motion signals corresponding to movement of the wrist 70, which may be associated with walking.

In some embodiments, the patient-worn monitor 60 may be operatively coupled to the PPG sensor 14. For example, the patient-worn monitor 60 may be coupled to the PPG sensor 14 via a cable 72. In some embodiments, the patient-worn monitor 60 may communicate wirelessly with the PPG sensor 14. In particular, in embodiments in which the patient-worn monitor 60 includes the controller 12, the patient-worn monitor 60 may receive and process PPG signals from the PPG sensor 14 to calculate one or more physiological parameters.

Further, in some embodiments, a motion sensor 16 (e.g., the motion sensor 16*b*) may be disposed in a housing 74 of the PPG sensor 14. As such, the motion sensor 16*b* may generate motion signals corresponding to movement of the body part to which the housing 74 is secured. For example, the housing 74 may be secured about a digit 76 of the patient 66. In some embodiments, the housing 74 may be secured to the forehead, an ear, the chest, the stomach, or any other suitable location about the patient 66. In the illustrated embodiment, the motion sensor 16*b* may generate motion signals corresponding to movement of the digit 76 and/or the hand of the patient 66, which may be associated with walking, tapping, and/or bending. The motion sensor 16*b* in the housing 74 of the PPG sensor 14 may generate motion signals that are more accurate or more indicative of movement of the housing 74 of the PPG sensor 14 relative to the patient's tissue as compared to motion sensors 16 that are located outside of the housing 74. Patient motion that causes movement of the housing 74 of the PPG sensor 14 relative to the patient's tissue may reduce the accuracy of physiological parameters calculated from the PPG signal. Accordingly, the motion sensor 16*b* may be desirable to detect such patient motion.

As such, in some embodiments, the system 10 may include two or more motion sensors 16 (e.g., the motion sensor 16a and the motion sensor 16b). Additionally, the two or more motion sensors 16 may be disposed in different housings (e.g., the housing 62 and the housing 74) and may be disposed in different locations, such as different locations about the patient 66 (e.g., the wrist 70 and the digit 76). Further, in some embodiments, the two or more motion sensors 16 may generate different types of motion signals. By way of example, the motion sensor 16a may generate motion signals related to the acceleration and/or velocity of the wrist 70 in three dimensions, and the motion sensor 16b may generate motion signals related to acceleration and/or velocity of the digit 76 in one or two dimensions.

Figure 3:
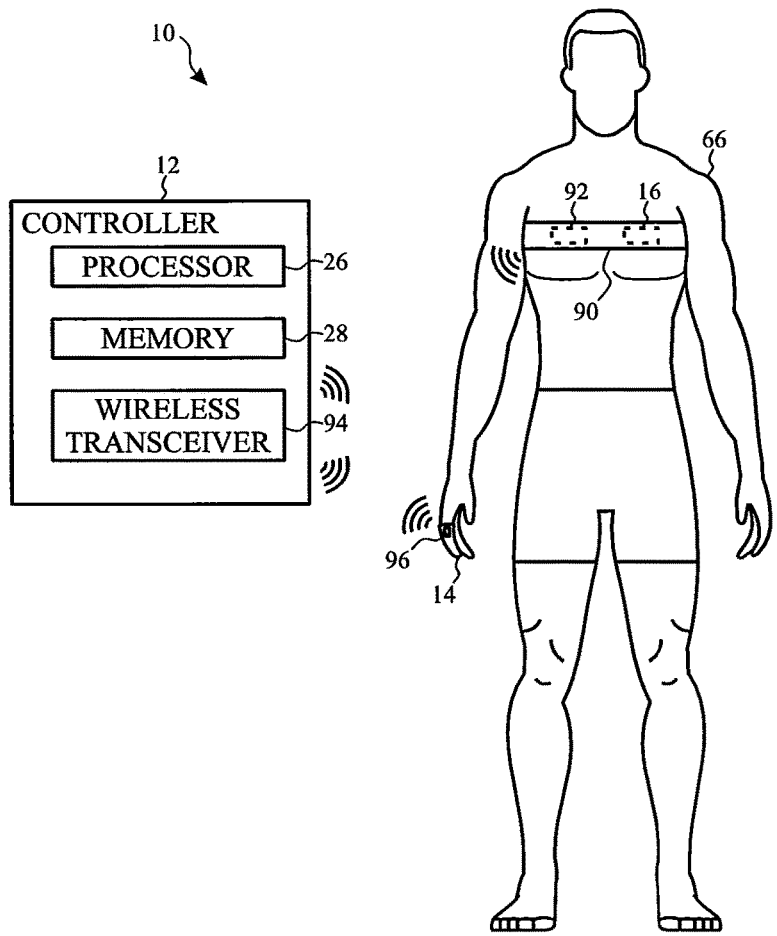
FIG. 3 is a schematic diagram of a PPG sensor disposed on a patient and a motion sensor disposed in a patient-worn article coupled to the patient, in accordance with an embodiment of the present disclosure.

As illustrated in FIG. 3, one or more motion sensors 16 may be disposed in one or more patient-worn articles 90. For example, the one or more patient-worn articles 90 may include a strap (e.g., a wrist strap, a chest strap, an ankle strap, a Zephyr™ BioHarness™), a bracelet, clothing, a garment, a harness, a ring, a necklace, etc. The one or more patient-worn articles 90 may be configured to wrap around or otherwise attach to a body part of the patient 66 such as, for example, a wrist, an arm, an ankle, the chest, the forehead, or the like. In some embodiments, the motion sensor 16 may include or may be operatively coupled to a wireless transceiver 92, which may transmit data (e.g., motion signals) to and receive data from a wireless transceiver 94 of the controller 12. In certain embodiments, the PPG sensor 14 may also include a wireless transceiver 96, which may transmit data to and receive data from the wireless transceiver 94 of the controller 12. The wireless transceivers 92, 94, and 96 may be configured to establish wireless communication using any suitable protocol. By way of example, the wireless transceivers 92, 94, and 96 may be configured to communicate using the IEEE 802.15.4 standard, and may communicate, for example, using ZigBee, WirelessHART, or MiWi protocols. Additionally or alternatively, the wireless transceivers 92, 94, and 96 may be configured to communicate using the Bluetooth standard or one or more of the IEEE 802.11 standards.

Figure 4:
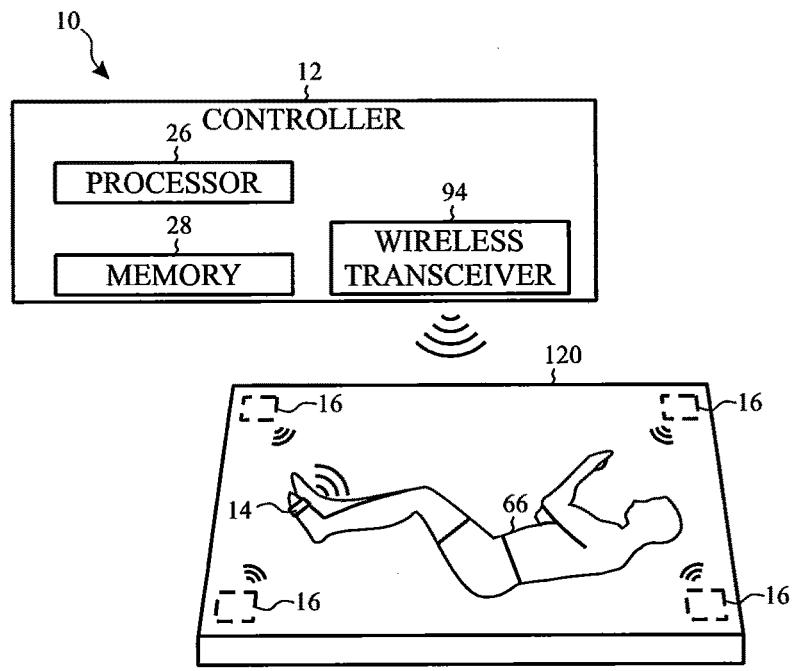
FIG. 4 is a schematic diagram of a patient device including a motion sensor and a PPG sensor disposed on a patient, in accordance with an embodiment of the present disclosure.

In some embodiments, one or more of the motion sensors 16 may not be coupled to the patient 66. For example, FIG. 4 illustrates an embodiment of the system 10 in which one or more motion sensors 16 are disposed in a patient device 120. In the illustrated embodiment, the patient device 120 is a patient bed. However, the patient device 120 may be a wheelchair, a blanket, a pillow, or any other suitable device configured to contact the patient 66. For example, the one or more motion sensors 16 in the patient device 120 may generate motion signals in response to movement of the patient 66 in the patient device 120, such as rolling, stretching, kicking, and so forth. In some embodiments, the one or more motion sensors 16 in the patient device 120 may include piezoelectric devices configured to generate motion signals in response to changes in pressure. As described in detail above, the controller 12 may receive motion signals from the one or more motion sensors 16 and may adaptively suppress PPG signal acquisition from the PPG sensor 14 based at least in part on the motion signals.

Figure 5:
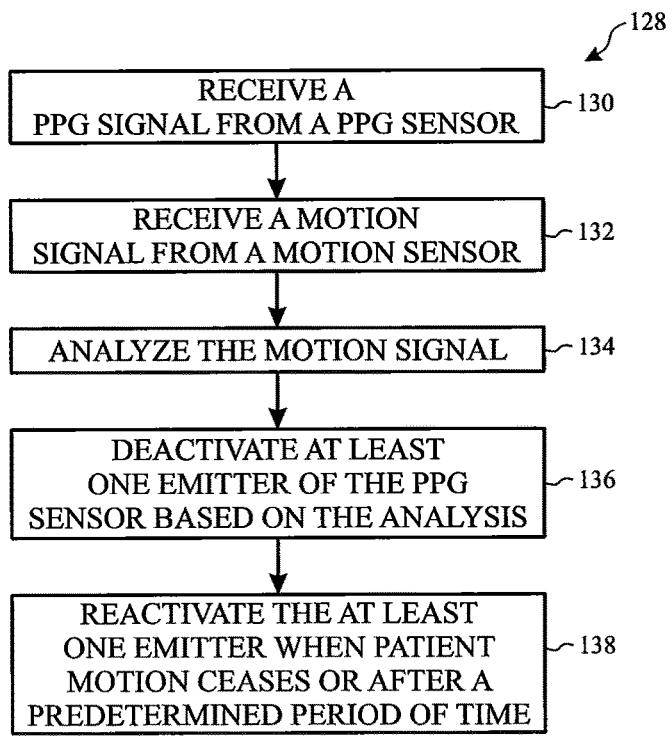
FIG. 5 is a flow diagram of a method for adaptively suppressing PPG signal acquisition based on an analysis of a motion signal, in accordance with an embodiment of the present disclosure.
Figure 6:
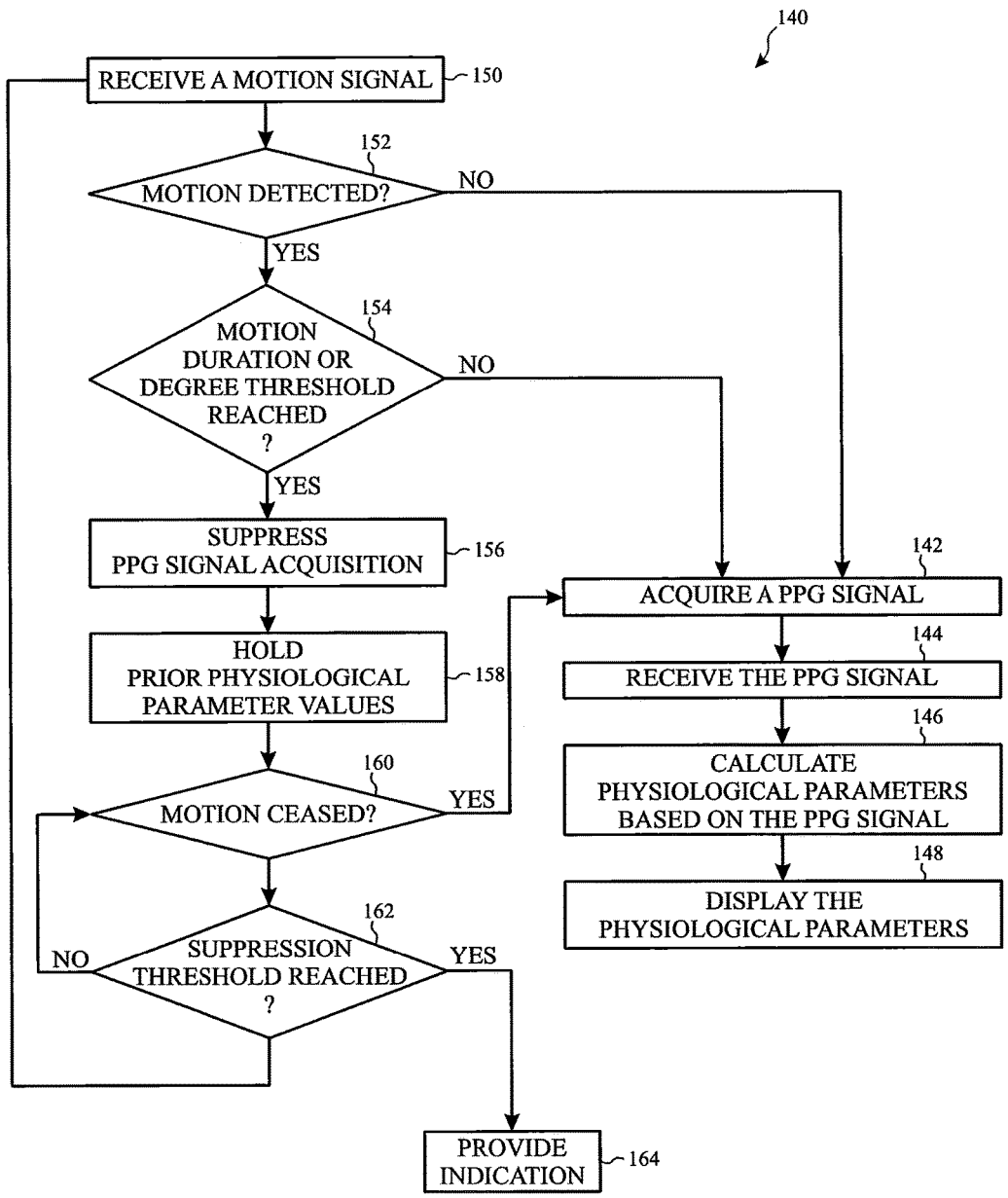
FIG. 6 is a flow diagram of a method for adaptively suppressing PPG signal acquisition based on a motion signal and one or more thresholds, in accordance with an embodiment of the present disclosure.
Figure 7:
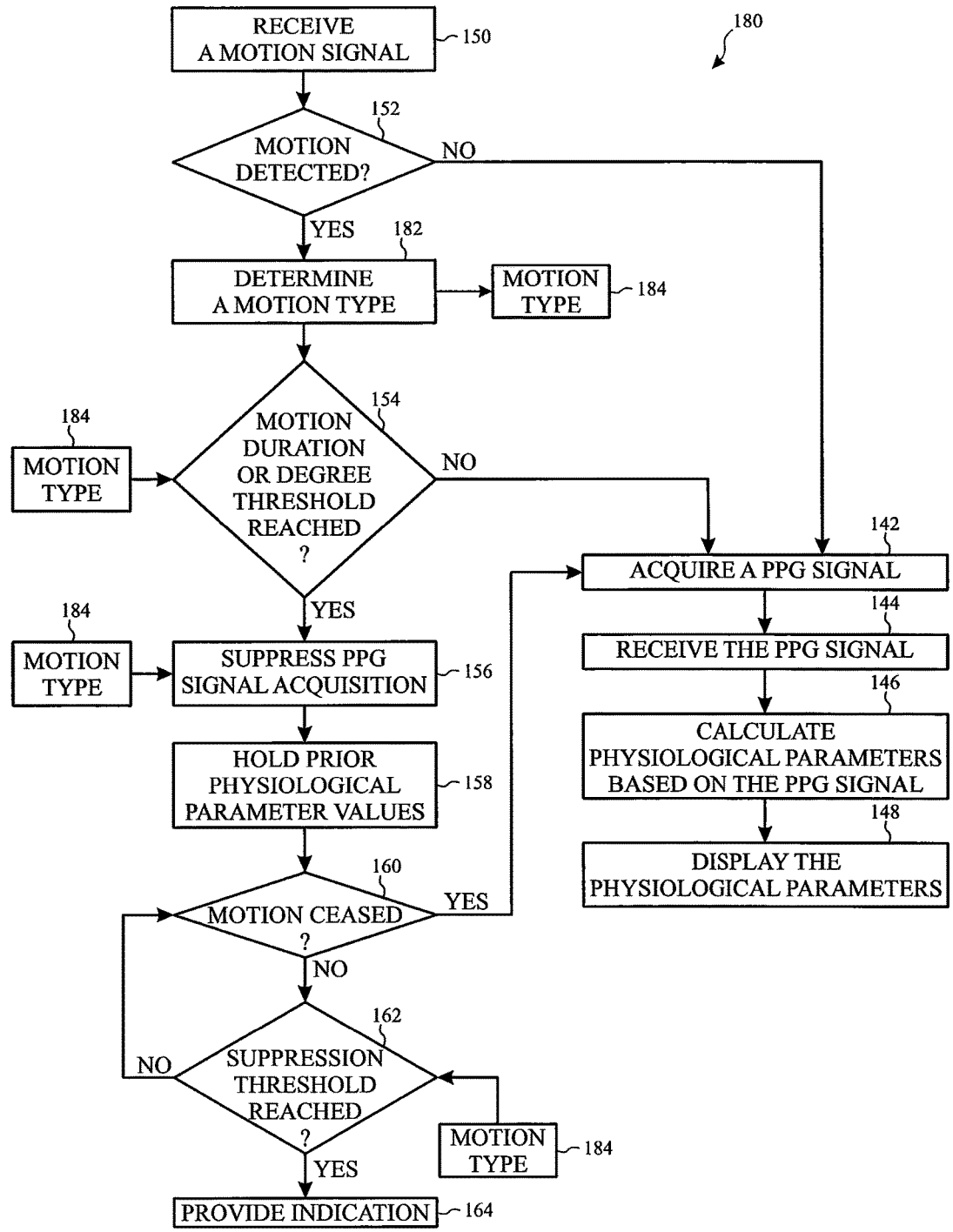
FIG. 7 is a flow diagram of a method for adaptively suppressing PPG signal acquisition based on a type of patient motion, in accordance with an embodiment of the present disclosure.
Figure 8:
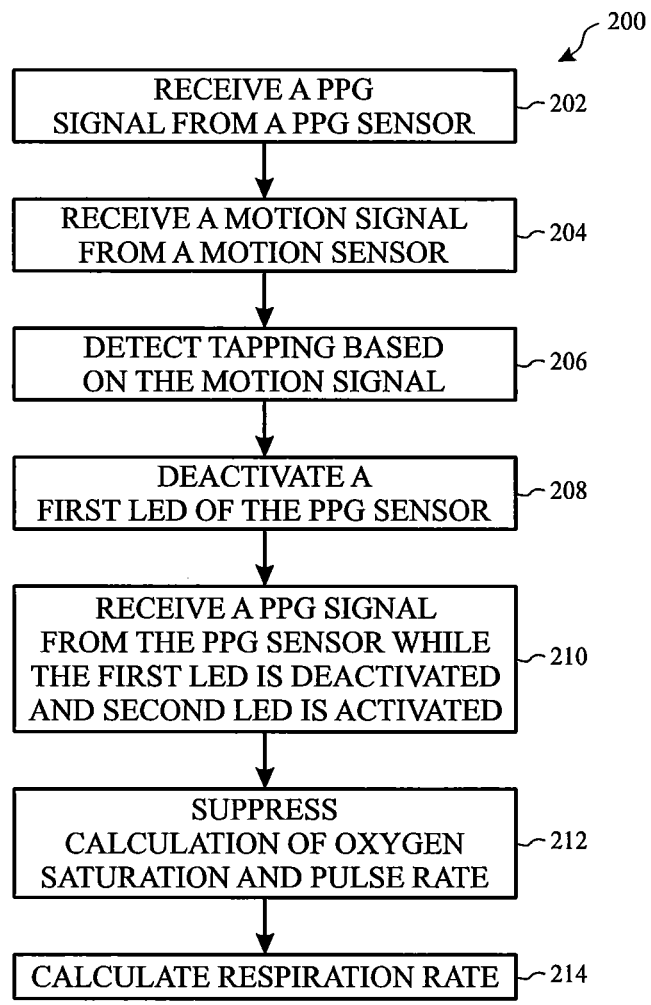
FIG. 8 is a flow diagram of a method for adaptively suppressing PPG signal acquisition in response to a detection of a tapping motion, in accordance with an embodiment of the present disclosure.
Figure 9:
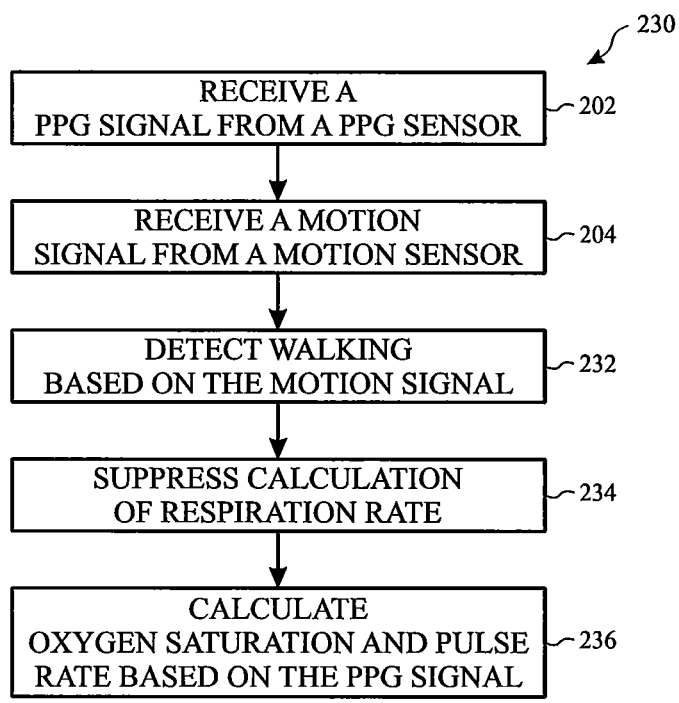
FIG. 9 is a flow diagram of a method for adaptively suppressing PPG signal processing in response to a detection of a walking motion, in accordance with an embodiment of the present disclosure.

The present embodiments also provide various methods for suppressing PPG signal acquisition and/or processing during patient motion. For example, FIGS. 5 and 6 illustrate methods for suppressing PPG signal acquisition, FIGS. 7 and 8 illustrate methods for suppressing PPG signal acquisition based on the type of patient motion, and FIG. 9 illustrates a method for suppressing PPG signal processing based on the type of patient motion. The methods of FIGS. 5-9 may be performed as an automated procedure by a system, such as the system 10. Additionally, certain steps of the methods of FIGS. 5-9 may be performed by a processor, such as the processor 26, or a processor-based device, such as the controller 12 that includes instructions for implementing certain steps of the methods. Further, it should be noted that the steps of the methods of FIGS. 5-9 may be performed in any suitable order and in any suitable combination.

With the foregoing in mind, FIG. 5 illustrates a method 128 for suppressing PPG signal acquisition based on an analysis of a motion signal. The method 128 may include receiving (e.g., via the processor 26) a PPG signal from a PPG sensor (e.g., the PPG sensor 14) (block 130). Additionally, the method 128 may include receiving (e.g., via the processor 26) a motion signal from a motion sensor (e.g., the motion sensor 16) (block 132). Further, the method 128 may include analyzing (e.g., via the processor 26) the motion signal (block 134). For example, as described in detail above, the processor 26 may analyze the motion signal to detect patient motion, to determine a degree of patient motion, to determine a duration of patient motion, to determine a type of patient motion, or a combination thereof. Additionally, the method 128 may include deactivating (e.g., via the processor 26) at least one emitter (e.g., the emitter 18) of the PPG sensor based on the analysis (block 136). For example, as described in detail above, the processor 26 may deactivate one or both of the LEDs 22 and 24 based on the degree of patient motion, the duration of patient motion, the type of patient motion, or a combination thereof. Additionally, in some embodiments, the method 128 may include reactivating (e.g., via the processor 26) the at least one emitter when patient motion has ceased and/or after a predetermined period of time (block 138). For example, if the patient motion still violates a threshold, the processor 26 may reactivate the emitter when the predetermined period of time reaches a suppression threshold so that an old PPG signal or prior physiological parameter values are not relied on for too long.

In some embodiments, the processor 26 may determine that patient motion has ceased in response to a determination that there is no patient motion (e.g., the patient motion or motion signal is less than the motion threshold), a determination that a degree of patient motion is less than the degree threshold, and/or a determination that a duration of patient motion is less than the duration threshold. Further, in some embodiments, the processor 26 may determine that patient motion has ceased in response to a determination that there is no patient motion (e.g., the patient motion or motion signal is less than the motion threshold) for an amount of time exceeding a cessation threshold or in response to a determination that a degree of patient motion is less than the degree threshold for an amount of time exceeding a cessation threshold. For example, the cessation threshold may be between approximately 5 seconds and 5 minutes, 15 seconds and 2 minutes, 30 seconds and 1 minute, or any other suitable amount of time. That is, in some embodiments, the processor 26 may not reactivate the at least one emitter immediately, but may reactivate the at least one emitter after the patient motion has been stable for a while.

FIG. 6 illustrates a method 140 for suppressing PPG signal acquisition based on a comparison of a motion signal to one or more thresholds. The method 140 includes acquiring a photoplethysmograph (PPG) signal (block 142). For example, the PPG sensor 14 may acquire the PPG signal by emitting light into a patient's tissue using the one or more emitters 18 (e.g., the LEDs 22 and 24) and detected returned light after interaction with the patient's tissue using the detector 20. In some embodiments, the controller 12 may also be used to acquire the PPG signal by providing power to the PPG signal 14 (e.g., the one or more emitters 18) and/or by providing a drive signal using the light drive 50 to selectively active the one or more emitters 18. Additionally, the method 140 may include receiving (e.g., via the controller 12) the PPG signal (block 144). For example, the controller 12 may receive the PPG signal from the PPG sensor 14. Further, the method 140 may include calculating (e.g., via the processor 26) one or more physiological parameters based at least in part on the PPG signal (block 146) and displaying (e.g., via the display 32) the one or more physiological parameters (block 148). For example, the processor 26 may periodically or continuously calculate and display values of the one or more physiological parameters based on the received PPG signal.

Additionally, the method 140 may include receiving (e.g., via the controller 12) a motion signal (block 150). For example, the controller 12 may receive one or more motion signals from one or more motion sensors 16. Further, the method 140 may include determining (e.g., via the processor 26) if patient motion is detected based on the motion signal (query 152). For example, the processor 26 may analyze a raw or filtered motion signal or may decompose the motion signal into component parts using any of the processing techniques described in detail above. In some embodiments, the processor 26 may process the motion signal to determine a displacement signal, a velocity signal, and/or an acceleration signal. The processor 26 may compare the motion signal (e.g., raw, processed, or component parts) to one or more motion thresholds and/or one or more motion profiles stored in the memory 28, as described in detail above, and may detect patient motion based on the comparison. If patient motion is not detected, the method 140 may continue acquiring the PPG signal (block 142), receiving the PPG signal (block 144), calculating the one or more physiological parameters based on the PPG signal (block 146), and displaying the one or more physiological parameters (block 148).

If patient motion is detected, the method 140 may include determining whether a motion duration threshold or a motion degree threshold is reached (query 154). For example, the processor 26 may compare the motion signal to a motion degree threshold (e.g., motion severity threshold), which may be stored in the memory 28, and may determine that the motion degree threshold is reached if the motion signal exceeds the motion degree threshold. In some embodiments, the processor 28 may compare the motion signal to one or more motion profiles to determine the degree of motion (e.g., severity of motion) and may compare the degree of motion to the motion degree threshold. In certain embodiments, even if the motion degree threshold is not met, the processor 26 may determine that the motion duration threshold is reached if the motion signal exceeds a motion threshold (e.g., a motion threshold for detecting patient motion or any other suitable threshold) for a duration of time exceeding the duration threshold. If the motion duration threshold and the motion degree threshold have not been reached, the method 140 may continue acquiring the PPG signal (block 142), receiving the PPG signal (block 144), calculating the one or more physiological parameters based on the PPG signal (block 146), and displaying the one or more physiological parameters (block 148).

If the motion degree threshold or the motion duration threshold is reached, the method 140 may include suppressing (e.g., via the controller 12) PPG signal acquisition (block 156). In particular, the controller 12 may suppress PPG signal acquisition by turning off or deactivating one or more emitters 18 (e.g., one or both of the LEDs 22 and 24) of the PPG sensor 14. In some embodiments, the controller 12 may turn off or deactivate one or more emitters 18 by suppressing or halting flow of power from the power source 42 to the one or more emitters 18. In certain embodiments, the controller 12 may control the switch 44 (e.g., the first switch 46 and/or the second switch 48) to suppress or halt flow of power from the power source 42 to the one or more emitters 18. Further, in some embodiments, the controller 12 may turn off or deactivate one or more emitters 18 may modifying or suppressing the drive signal from the light drive 50.

In some embodiments, the method 140 may include holding (e.g., via the controller 12) one or more values of the one or more physiological parameters on the display (e.g., the display 32) (block 158). That is, the controller 12 may cause the display 32 to hold prior values of the physiological parameters that were determined from the PPG signal when PPG signal acquisition was not suppressed. For example, the controller 12 may cause the display 32 to hold values of the physiological parameters that were displayed when the controller 12 determined that PPG signal acquisition should be suppressed based on patient motion. Moreover, by holding prior values of the physiological parameters, the controller 12 may stop processing the PPG signal to calculate new or updated values of the physiological parameters. As such, the controller 12 may also suppress PPG signal processing.

In certain embodiments, the method 140 may include determining (e.g., via the processor 26) whether patient motion has ceased (query 160). For example, the processor 26 may continue analyzing the motions signal while PPG signal acquisition is suppressed and may determine that patient motion has ceased based on a determination that the motion signal is below the motion threshold, the motion duration threshold, and/or the motion degree threshold. Further, as noted above, in some embodiments, the processor 26 may determine that patient motion has ceased based on a determination that the motion signal is less than the motion threshold for a period of time exceeding a cessation threshold or based on a determination that a degree of the motion signal is less than the motion degree threshold for a period of time exceeding the cessation threshold. If the patient motion has ceased, the controller 12 may stop suppressing the PPG signal acquisition (block 156) and may continue acquiring the PPG signal (block 142), receiving the PPG signal (block 144), calculating the one or more physiological parameters based on the PPG signal (block 146), and displaying the one or more physiological parameters (block 148).

If the patient motion has not ceased, the method 140 may include determining (e.g., via the processor 26) whether a suppression threshold is reached (query 162). For example, the processor 26 may compare an amount of time that the PPG signal acquisition has been suppressed to the suppression threshold and may determine that the suppression threshold is reached when the amount of time exceeds the suppression threshold. As set forth above, the suppression threshold may be stored in the memory 28 and/or determined by the processor 26. If the suppression threshold has not been reached, the processor 26 may continue determining whether patient motion has ceased (block 160). Further, if the suppression threshold has been reached, the controller 12 may stop suppressing the PPG signal acquisition (block 156) and may continue acquiring the PPG signal (block 142) and the motion signal (block 150). In some embodiments, the method 140 may include providing (e.g., via the processor 26) an indication that a duration of patient motion exceeded a suppression threshold (block 164). For example, the processor 26 may cause the display 32 to display the indication.

For example, FIG. 7 illustrates a method 180 for adaptively suppressing PPG signal acquisition based on a type of patient motion. The method 180 may include acquiring the PPG signal (block 142), receiving the PPG signal (block 144), calculating the one or more physiological parameters based on the PPG signal (block 146), and displaying the one or more physiological parameters (block 148), as described above in FIG. 5. Additionally, the method 180 may include receiving the motion signal (block 150) and determining whether patient motion is detected (block 152). Additionally, the method 180 may include determining (e.g., via the processor 26) the type of motion (block 182). The determination step may output the motion type (block 184). The motion type (block 184) may include walking, tapping (e.g., tapping on the PPG sensor 14), bending (e.g., bending of the tissue site proximate to the PPG sensor 14), rolling (e.g., rolling over in bed), kicking, and the like. The processor 26 may determine the motion type (block 184) using any of the processing techniques described above with respect to FIG. 1.

Additionally, the method 180 may include determining whether the motion duration threshold and/or the motion degree threshold is reached (query 154). As illustrated, the motion type (block 184) may be used in the determination of whether the motion duration threshold and/or the motion degree threshold is reached. In particular, the motion type (block 184) may be used by the processor 26 to select a motion duration threshold and/or a motion degree threshold from the memory 26. In some embodiments, the processor 26 may also use information about the motion sensor 16, the PPG sensor 14, and/or the patient to select an appropriate threshold from the memory 28. Further, the method 180 may include suppressing PPG signal acquisition (block 156) if the motion duration or motion degree threshold is reached. In some embodiments, the type of patient motion (block 184) may be used as an input for suppressing PPG signal acquisition (block 156). For example, the processor 26 may determine whether to deactivate one or both LEDs 22 and 24 based on the type of patient motion. The method 180 may also include holding the one or more values of the one or more physiological parameters on the display (block 158) and determining whether motion ceased (query 160).

Further, the method 180 may include determining whether the suppression threshold is reached (query 162). As illustrated, the motion type (block 184) may be an input for the determination of whether the suppression threshold is reached (query 162). In particular, the processor 26 may use the motion type (block 184) to determine a suppression threshold. As noted above, the memory 28 may store different suppression thresholds for different types of patient motion, and the processor 26 may use the motion type (block 184) to select an appropriate suppression threshold. For example, walking may be considered "good" patient motion and may have a greater (e.g., longer) suppression threshold than other types of patient motion, such as tapping or bending, for example. In some embodiments, rolling and/or kicking in bed may be considered "good" patient motion (e.g., may be associated with healthy movement of a neonate) and may have a greater (e.g., longer) suppression threshold than other types of patient motion, such as tapping or bending, for example. In some embodiments, the processor 26 may also use information about the motion sensor 16, the PPG sensor 14, and/or the patient to select an appropriate suppression threshold from the memory 28. In some embodiments, the method 180 may include providing an indication that a duration of patient motion exceeded the suppression threshold (block 164), as described above in FIG. 5.

FIG. 8 illustrates a method 200 for adaptively suppressing PPG signal acquisition and processing in response to a determination that the motion type is tapping (e.g., tapping on the PPG sensor 14). As noted above, tapping may have a high negative effect on the accuracy of the algorithms for calculating oxygen saturation and pulse rate, but may have a low or no negative effect on the algorithm for calculating respiration rate. The method 200 may include receiving a PPG signal from a PPG sensor (block 202) and receiving a motion signal from a motion sensor (block 204). For example, the processor 26 may receive the PPG signal from the PPG sensor 14 and may receive the motion signal from the motion sensor 16. Additionally, the method 200 may include detecting tapping based on the motion signal (block 206). For example, the processor 26 may detect tapping from the motion signal using any of the processing techniques and/or the motion profiles described in detail above. The method 200 may also include deactivating a first LED (e.g., the red LED 22 or the infrared LED 24) of the PPG sensor in response to the detection of tapping (block 208). Additionally, the method 200 may include receiving a PPG signal from the PPG sensor that is generated while the first LED is deactivated (i.e., not emitting) and the second LED is activated (i.e., emitting) (block 210). Further, the method 200 may include suppressing calculation of oxygen saturation and pulse rate (block 212). For example, oxygen saturation and pulse rate may be calculated based on a PPG signal generated in response to light emitted from both LEDs 22 and 24. Accordingly, the processor 26 may suppress PPG processing and/or algorithms used to calculate oxygen saturation and pulse rate when the PPG signal is generated based on light emitted from only one LED. However, respiration rate may be calculated from a PPG signal generated in response to light emitted from only one LED. Accordingly, in some embodiments, the method 200 may include calculating respiration rate (block 214). For example, the processor 26 may calculate respiration rate using the PPG signal generated while the first LED is deactivated and the second LED is activated.

FIG. 9 illustrates a method 230 for adaptively suppressing PPG signal processing in response to a determination that the motion type is walking. As noted above, walking may have a high negative effect on the accuracy of the algorithm for calculating respiration rate, but may have a low or no negative effect on the algorithms for calculating oxygen saturation and pulse rate. The method 230 may include receiving a PPG signal from a PPG sensor (block 202) and receiving a motion signal from a motion sensor (block 204). The method 230 may also include detecting walking based on the motion signal (block 232). Further, the method 230 may include suppressing calculation of respiration rate (block 234). For example, the processor 26 may not process the PPG signal for the calculation of respiration rate and/or may not implement the algorithms for calculating respiration rate based on the PPG signal. Additionally, the method 230 may include calculating oxygen saturation and pulse rate (block 236). For example, the processor 26 may process the PPG signal for the calculation of oxygen saturation and pulse rate and may implement the algorithms for calculating respiration rate and pulse rate based on the PPG signal.

As described in detail above, the controller 12 may adaptively suppress PPG signal acquisition and/or processing based on patient motion detected by a motion sensor 16. In some embodiments, the controller 12 may additionally or alternatively adaptively suppress PPG signal acquisition and/or processing based on signal interference in the PPG signal. The signal interference may be ambient light interference and/or interference from other medical devices, cables, and so forth. The signal interference may distort and/or decrease the signal quality of the PPG signal. In some situations, ambient light interference may occur due to patient motion. For example, flexing or bending of the tissue proximate to a PPG sensor 14 may move the tissue with respect to the PPG sensor 14, and the movement may create a space between the PPG sensor 14 and the tissue that lets in ambient light. Accordingly, in some embodiments, the controller 12 may analyze the PPG signal to detect signal interference, such as ambient light interference, and may deactivate one or more LEDs of the PPG sensor 14 based on an analysis of the signal interference.

Figure 10:
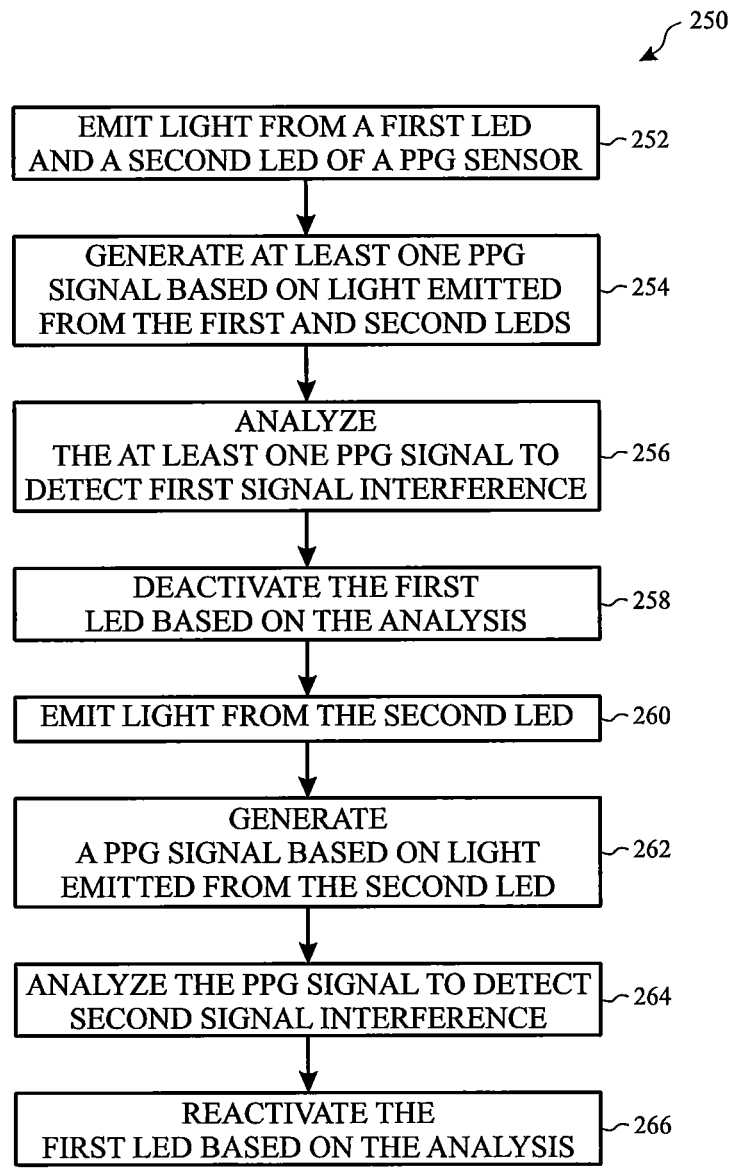
FIG. 10 is a flow diagram of a method for adaptively suppressing PPG signal acquisition based on an analysis of signal interference, in accordance with an embodiment of the present disclosure.

For example, FIG. 10 illustrates an embodiment of a method 250 for adaptively suppressing PPG signal acquisition based on signal interference. As illustrated, the method 250 may include emitting light from a first LED (e.g., the LED 22) and a second LED (e.g., the LED 24) of a PPG sensor (e.g., the PPG sensor 14) (block 252) and generating (e.g., via the detector 20) at least one PPG signal based on light emitted from the first and second LEDs 22 and 24 after interaction with a patient's tissue (block 254). In some embodiments, the detector 20 may generate two PPG signals based on light emitted from the first and second LEDs 22 and 24. For example, as noted above, the light driver 50 may provide a time-multiplexed drive signal to the first LED 22 (e.g., a red LED) and the second LED 24 (e.g., IR LED) to alternate activation of the first and second LEDs 22 and 24. In some embodiments, the light driver 50 may provide a time-multiplexed drive signal to activate the red LED 22 during red pulse width periods and the IR LED 24 during IR pulse width periods. Accordingly, the detector 20 may detect light emitted from the red LED 22 during the red pulse width periods and may generate a first PPG signal based on the detected light emitted from the red LED 22 during the red pulse width periods, and the detector 20 may detect light emitted from the IR LED 24 during the IR pulse width periods and may generate a second PPG signal based on the detected light emitted from the IR LED 24 during the IR pulse width periods. Further, in some embodiments, the time-multiplexed drive signal may deactivate both LEDs 22 and 24 during a dark period between the red and IR pulse width periods, and the detector 20 may generate a signal (e.g., a dark signal) during the dark periods to detect ambient light.

Further, the method 250 may include analyzing the at least one PPG signal to detect first signal interference (block 256). For example, the processor 26 may analyze the first PPG signal (e.g., detected light from the red LED 22 during red pulse width periods), the second PPG signal (e.g., detected light from the IR LED 24 during IR pulse width periods), or both. The processor 26 may determine one or more signal quality metrics, such as a signal-to-noise ratio, of the at least one PPG signal and may detect the first signal interference based on the signal quality metrics. Further, the processor 26 may detect one or more signal artifacts in the at least one PPG signal and may detect the first signal interference based on the presence of one or more signal artifacts. Additionally, in some embodiments, analyzing the at least PPG signal may include analyzing the dark signal. For example, the processor 26 may compare the first PPG signal and/or the second PPG signal to the dark signal to determine the first signal interference, such as ambient light interference.

Additionally, the method 250 may include deactivating the first LED (e.g., the LED 22) of the PPG sensor 14 and based on the analysis of the first signal interference (block 258). In some embodiments, the processor 26 may deactivate the first LED 22 and suppress calculation of physiological parameters from the first PPG signal based on the analysis. In certain embodiments, the processor 26 may deactivate the first LED 22 in response to a determination that a degree of the first signal interference exceeds a degree threshold (e.g., stored in the memory 28) and/or a duration of the first signal interference exceeds a duration threshold (e.g., stored in the memory 28). In some embodiments, the processor 26 may deactivate the first LED 22 if the signal-to-noise ratio (SNR) of the first PPG signal is less than a SNR ratio, which may be stored in the memory 28. Further, the processor 26 may deactivate the first LED 22 if a number of detected artifacts exceeds an artifact threshold, which may be stored in the memory 28. In particular, the signal interference may decrease the signal quality of the PPG signal, which may decrease the accuracy of physiological parameters calculated based on the PPG signal. Accordingly, the controller 12 may deactivate an LED of the PPG sensor 14 and may suppress calculation of physiological parameters based on the PPG signal during periods of signal interference. Thus, the controller 12 may reduce power consumption of the PPG sensor 14 associated with powering the LED and power consumption of the controller 12 associated with processing the PPG signal and calculating physiological parameters.

Further, the method 250 may include emitting light from the second LED (e.g., the LED 24) of the PPG sensor 14 (block 260) and generating (e.g., via the detector 20) a PPG signal based on light emitted from the LED 22 after interaction with a patient's tissue (block 262). The method 250 may also include analyzing the PPG signal to detect second signal interference (block 264) and reactivating the first LED 24 based on the analysis (block 266). For example, the processor 26 may analyze the PPG signal to determine when the signal interference has decreased to a desired extent to determine when the LED 22 may be reactivated. In some embodiments, the processor 26 may reactivate the first LED 22 in response to a determination that a degree of the second signal interference is less than a degree threshold (e.g., stored in the memory 28) and/or a duration of the second signal interference is less than a duration threshold (e.g., stored in the memory 28). In some embodiments, the processor 26 may reactivate the first LED 22 if the signal-to-noise ratio (SNR) of the PPG signal is greater than a SNR threshold and/or if a number of detected artifacts in the PPG signal is less than an artifact threshold. In certain embodiments, the processor 26 may reactivate the first LED 22 in response to a determination that the second signal interference has decreased to a desired extent (e.g., a degree of the second signal interference is less than a degree threshold, the SNR is greater than a SNR threshold, and/or a number of detected artifacts is less than an artifact threshold) for an amount of time exceeding a threshold. That is, the processor 26 may not reactivate the first LED 22 immediately, but when the second signal interference is stable for a period of time. Accordingly, after reactivating the first LED 22, the processor 26 may calculate physiological parameters based on a PPG signal generated when both LEDs 22 and 24 are emitting light.

The processors described above (e.g., the processor 26) may include multiple microprocessors, one or more "general-purpose" microprocessors, one or more special-purpose microprocessors, one or more application specific integrated circuits (ASICS), one or more reduced instruction set (RISC) processors, or some combination thereof. Additionally, the memory devices described above (e.g., the memory 28) may include a volatile memory, such as random access memory (RAM), and/or a nonvolatile memory, such as ROM. The memory 28 may include one or more tangible, non-transitory, machine-readable media collectively storing instructions executable by the processor 26 to perform the methods and control actions described herein. Such machine-readable media can be any available media that can be accessed by the processor 26 or by any general purpose or special purpose computer or other machine with a processor. The memory 28 may store a variety of information and may be used for various purposes. For example, the memory 28 may store processor-executable instructions (e.g., firmware or software) for the processor 26 to execute, such as instructions for carrying out any of the techniques discloses herein. The memory 28 (e.g., nonvolatile storage) may include read-only memory (ROM), flash memory, a hard drive, or any other suitable optical, magnetic, or solid-state storage medium, or a combination thereof. The memory 28 may store data (e.g., the PPG signal, the motion signal, etc.), instructions (e.g., software or firmware for processing the PPG signal and/or the motion signal, for determining the physiological parameters, a degree of motion, a duration of motion, a type of motion, etc., and/or taking appropriate remedial actions), predetermined thresholds, and any other suitable data.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that elements of the disclosed embodiments may be combined or exchanged with one another.

What is claimed is:

1. A system, comprising:
   a photoplethysmograph (PPG) sensor comprising at least one emitter comprising a first light emitting diode (LED) and a second LED that are configured to emit light into a tissue of a patient when activated and at least one detector configured to detect the light after interaction with the tissue and to generate a PPG signal based on the detected light;
   a motion sensor configured to generate a motion signal indicative of motion of the patient; and
   a processor configured to:
      receive the PPG signal from the PPG sensor and the motion signal from the motion sensor;
      process the PPG signal for a respiration rate, an oxygen saturation, and a pulse rate;
      analyze the motion signal to detect motion of the patient and to determine a type of motion of the patient;
      in response to detecting a first type of motion, calculate the oxygen saturation and the pulse rate based on the PPG signal and suppress processing of the PPG signal for the respiration rate, wherein the light detected by the detector to generate the PPG signal that is used to calculate the oxygen saturation and the pulse rate during detection of the first type of motion comprises light emitted from the first and second LEDs after interaction with the tissue; and
      in response to detecting a second type of motion, deactivate the first LED of the at least one emitter of the PPG sensor while the second LED of the at least one emitter remains activated, wherein the light detected by the detector to generate the PPG signal when the first LED is deactivated comprises light emitted from the second LED after interaction with the tissue, and wherein the processor is configured to calculate the respiration rate of the patient based on the PPG signal while the first LED is deactivated and the second LED is activated.

2. The system of claim 1, wherein the processor is configured to deactivate the first LED of the at least one emitter of the PPG sensor in response to a determination that the motion signal exceeds a motion threshold for a period of time that exceeds a duration threshold.

3. The system of claim 1, wherein the processor is configured to deactivate the first LED of the at least one emitter of the PPG sensor in response to a determination that the motion signal exceeds a motion degree threshold.

4. The system of claim 1, wherein the processor is configured to reactivate the first LED of the at least one emitter in response to a determination that motion of the patient has ceased or in response to a determination that the first LED of the at least one emitter has been deactivated for an amount of time that reaches a suppression threshold.

5. The system of claim 1, comprising a light drive coupled to the processor, wherein the light drive is configured to provide a drive signal to the first LED and the second LED of the at least one emitter to activate the first LED and the second LED of the at least one emitter, and wherein the processor is configured to control the light drive to control activation and deactivation of the first LED and the second LED of the at least one emitter.

6. The system of claim 1, comprising:
   a power source configured to power the at least one emitter; and
   a switch coupled to the power source and the at least one emitter, wherein the processor is configured to open the switch to deactivate the first LED of the at least one emitter and to close the switch to reactivate the first LED of the at least one emitter.

7. The system of claim 1, wherein the second type of motion is tapping on the PPG sensor.

8. The system of claim 1, wherein the motion sensor is disposed in a housing of the PPG sensor.

9. The system of claim 1, comprising a patient-worn pulse oximeter having the processor and the PPG sensor, wherein the patient-worn pulse oximeter is configured to calculate physiological parameters of the patient based on the PPG signal, and wherein the motion sensor is disposed in a housing of the patient-worn pulse oximeter.

10. The system of claim 1, wherein the motion sensor is disposed in a patient-worn article configured to be secured to the patient.

11. The system of claim 1, wherein the motion sensor is disposed in a patient bed.

12. A patient monitor, comprising:
   a memory encoding one or more processor-executable routines; and
   a processor configured to access and execute the one or more processor-executable routines encoded by the memory, wherein the one or more processor-executable routines, when executed, cause the processor to:

receive a photoplethysmograph (PPG) signal from a PPG sensor configured to be secured to a patient, wherein the PPG sensor comprises at least one emitter comprising a first light emitting diode (LED) and a second LED;

receive a motion signal indicative of motion of the patient from a motion sensor;

detect patient motion in response to a determination that the motion signal exceeds a motion threshold;

determine a type of the patient motion based on the motion signal; and deactivate a first light emitting diode (LED) of at least one emitter of the PPG sensor in response to a determination that the type of patient motion comprises tapping on the PPG sensor, a determination that a degree of the patient motion exceeds a motion degree threshold, and a determination that a duration of the patient motion exceeds a motion duration threshold; and calculate respiration rate based on the PPG signal generated while the second LED is activated.

13. The patient monitor of claim 12, wherein the memory stores a plurality of suppression thresholds and each suppression threshold of the plurality of suppression thresholds is associated with one type of patient motion, and wherein the one or more processor-executable routines, when executed, cause the processor to:

select a suppression threshold from the plurality of suppression thresholds stored in the memory based on the type of the patient motion;

deactivate the first LED of the at least one emitter of the PPG sensor for a period of time; and reactivate the first LED of the at least one emitter of the PPG sensor when the period of time reaches the suppression threshold.

14. The patient monitor of claim 12, wherein the memory stores a plurality of motion profiles and each motion profile of the plurality of motion profiles is associated with one type of patient motion, and wherein the one or more processor-executable routines, when executed, cause the processor to:

compare the motion signal to one or more motion profiles of the plurality of motion profiles stored in the memory; and determine the type of patient motion based on the comparison.

15. The patient monitor of claim 12, wherein the one or more processor-executable routines, when executed, cause the processor to open a switch disposed between a power source and the first LED of the at least one emitter of the PPG sensor to deactivate the first LED of the at least one emitter of the PPG sensor.

16. A system, comprising:

a photoplethysmograph (PPG) sensor comprising at least one emitter comprising a first light emitting diode (LED) and a second LED that are configured to emit light into a tissue of a patient when activated and at least one detector configured to detect the light after interaction with the tissue and to generate a PPG signal based on the detected light;

a motion sensor configured to generate a motion signal indicative of motion of the patient; and a processor configured to:

receive the PPG signal from the PPG sensor and the motion signal from the motion sensor;

process the PPG signal for a respiration rate, an oxygen saturation, and a pulse rate;

analyze the motion signal to determine a type of motion of the patient; and in response to a determination that the type of motion is tapping on the PPG sensor, deactivate the first LED of the at least one emitter of the PPG sensor while the second LED of the at least one emitter remains activated, wherein the light detected by the detector to generate the PPG signal when the first LED is deactivated comprises light emitted from the second LED after interaction with the tissue, and wherein the processor is configured to calculate the respiration rate of the patient based on the PPG signal while the first LED is deactivated and the second LED is activated and to suppress processing of the PPG signal for an oxygen saturation calculation and a pulse rate calculation while the first LED is deactivated and the second LED is activated.

* * * * *